US012688937B2

(12) United States Patent
Shimizu

(10) Patent No.: US 12,688,937 B2
(45) Date of Patent: Jul. 21, 2026

(54) BIOMETRIC INFORMATION ACQUISITION DEVICE

(71) Applicant: SEIKO EPSON CORPORATION, Tokyo (JP)

(72) Inventor: Satoshi Shimizu, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 94 days.

(21) Appl. No.: 18/733,921

(22) Filed: Jun. 5, 2024

(65) Prior Publication Data

US 2024/0404696 A1     Dec. 5, 2024

(30) Foreign Application Priority Data

Jun. 5, 2023     (JP) .................................. 2023-092448

(51) Int. Cl.
G16H 40/67          (2018.01)
G01N 21/3581          (2014.01)

(52) U.S. Cl.
CPC ......... G16H 40/67 (2018.01); G01N 21/3581 (2013.01)

(58) Field of Classification Search
CPC ........................... G16H 40/67; G01N 21/3581
See application file for complete search history.

(56) References Cited

U.S. PATENT DOCUMENTS

| | | | | |
|---|---|---|---|---|
| 2013/0137941 A1* | 5/2013 | Schardey | ............... | A61B 5/024 600/483 |
| 2014/0135612 A1* | 5/2014 | Yuen | .................... | A61B 5/6838 600/407 |
| 2018/0110450 A1* | 4/2018 | Lamego | ............... | A61B 5/0022 |
| 2021/0321953 A1* | 10/2021 | Panneer Selvam | .... | A61B 5/681 |
| 2023/0389832 A1* | 12/2023 | Li | ................... | H04M 1/724094 |

FOREIGN PATENT DOCUMENTS

| | | |
|---|---|---|
| EP | 3554366 A1 | 10/2019 |
| JP | 2022153480 A | 10/2022 |

* cited by examiner

*Primary Examiner* — Michelle M Iacoletti
*Assistant Examiner* — Mohamed Doumbia
(74) *Attorney, Agent, or Firm* — CHIP LAW GROUP

(57)          ABSTRACT

A biometric information acquisition device includes an acquisition section that obtains first information based on a light amount of the red light received by the first light receiving element, second information based on a light amount of the infrared light received by the second light receiving element, and third information based on a light amount of the green light received by the third light receiving element; and the drive control section that controls a drive and a stop of each of the first light emitting element, the second light emitting element, and the third light emitting element; wherein the biometric information acquisition device measures first biometric information based on the first information and the second information, and second biometric information based on the third information, and the drive control section performs at least one of a first process, which stops the light emission of the first light emitting element and the second light emitting element when a measurement period for measuring the first biometric information reaches the first time period T1, and a second process, which stops the light emission of the third light emitting element when the measurement period for measuring the second biometric information reaches the second time period T2.

5 Claims, 3 Drawing Sheets

BIOMETRIC INFORMATION ACQUISITION DEVICE

The present application is based on, and claims priority from JP Application Serial Number 2023-092448, filed Jun. 5, 2023, the disclosure of which is hereby incorporated by reference herein in its entirety.

BACKGROUND

1. Technical Field

The present disclosure relates to a biometric information acquisition device.

2. Related Art

In recent years, various wearable terminal devices have been used to monitor biological information. These wearable terminal devices have, for example, a light source and a light receiving element, as shown in JP-A-2022-153480. Light emitted from the light source penetrates a living body, and the light receiving element receives the penetrating light. The wearable terminal device shown in JP-A-2022-153480 obtains biological information such as pulse wave and blood oxygen saturation concentration based on the amount of light received by the light receiving element. In order to obtain accurate data, such biological information is desirably obtained by continuously emitting light from the light source and by continuously receiving the light with the light receiving element for a predetermined time period.

However, in the related art method, the light source continues to emit light and the light receiving element continues to receive light even after a predetermined time period has passed. Thus, there is a problem that power consumption increases.

SUMMARY

The biometric information acquisition device of the present disclosure includes a light emitting unit having a first light emitting element that emits red light toward a living body, a second light emitting element that emits infrared light toward the living body, and a third light emitting element that emits green light toward the living body; a light receiving unit having a first light receiving element that receives the red light that passed through the living body, a second light receiving element that receives the infrared light that passed through the living body, and a third light receiving element that receives the green light that passed through the living body; an acquisition section that obtains first information based on a light amount of the red light received by the first light receiving element, second information based on a light amount of the infrared light received by the second light receiving element, and third information based on a light amount of the green light received by the third light receiving element; and a drive control section that controls drive and stop of each of the first light emitting element, the second light emitting element, and the third light emitting element, wherein the biometric information acquisition device measures first biometric information based on the first information and the second information, and second biometric information based on the third information, and the drive control section performs at least one of a first process, which stops the light emission of the first light emitting element and the second light emitting element when a measurement t period for measuring the first biometric information reaches a first time period T1, and a second process, which stops the light emission of the third light emitting element when the measurement period for measuring the second biometric information reaches a second time period T2.

DESCRIPTION OF EMBODIMENTS

Hereinafter, a biometric information acquisition device of the present disclosure will be described in detail based on suitable embodiments shown in the accompanying drawings.

Embodiment

Figure 1:
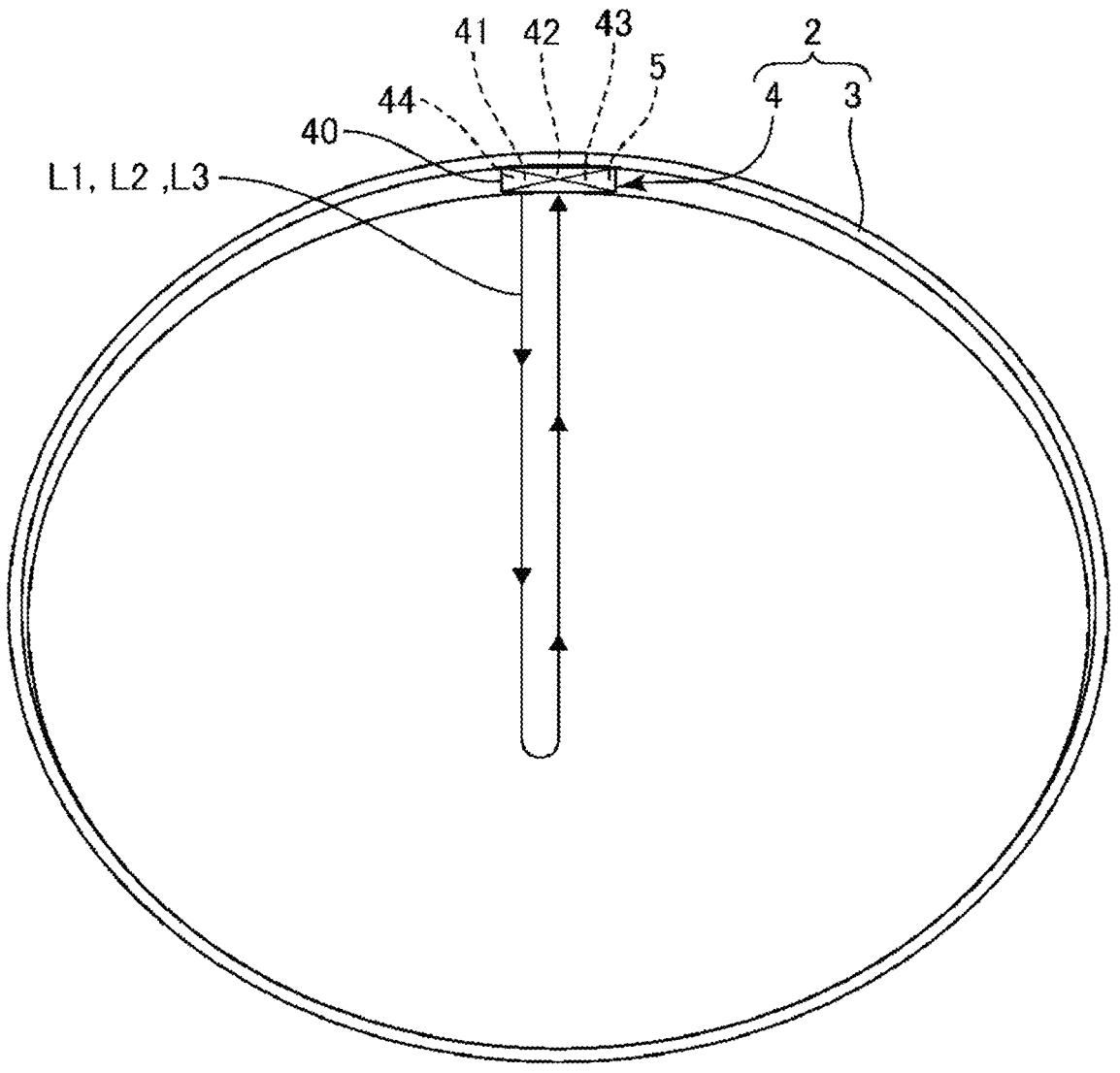
FIG. 1 is a cross-sectional view of a biometric information acquisition device of the present disclosure.
Figure 2:
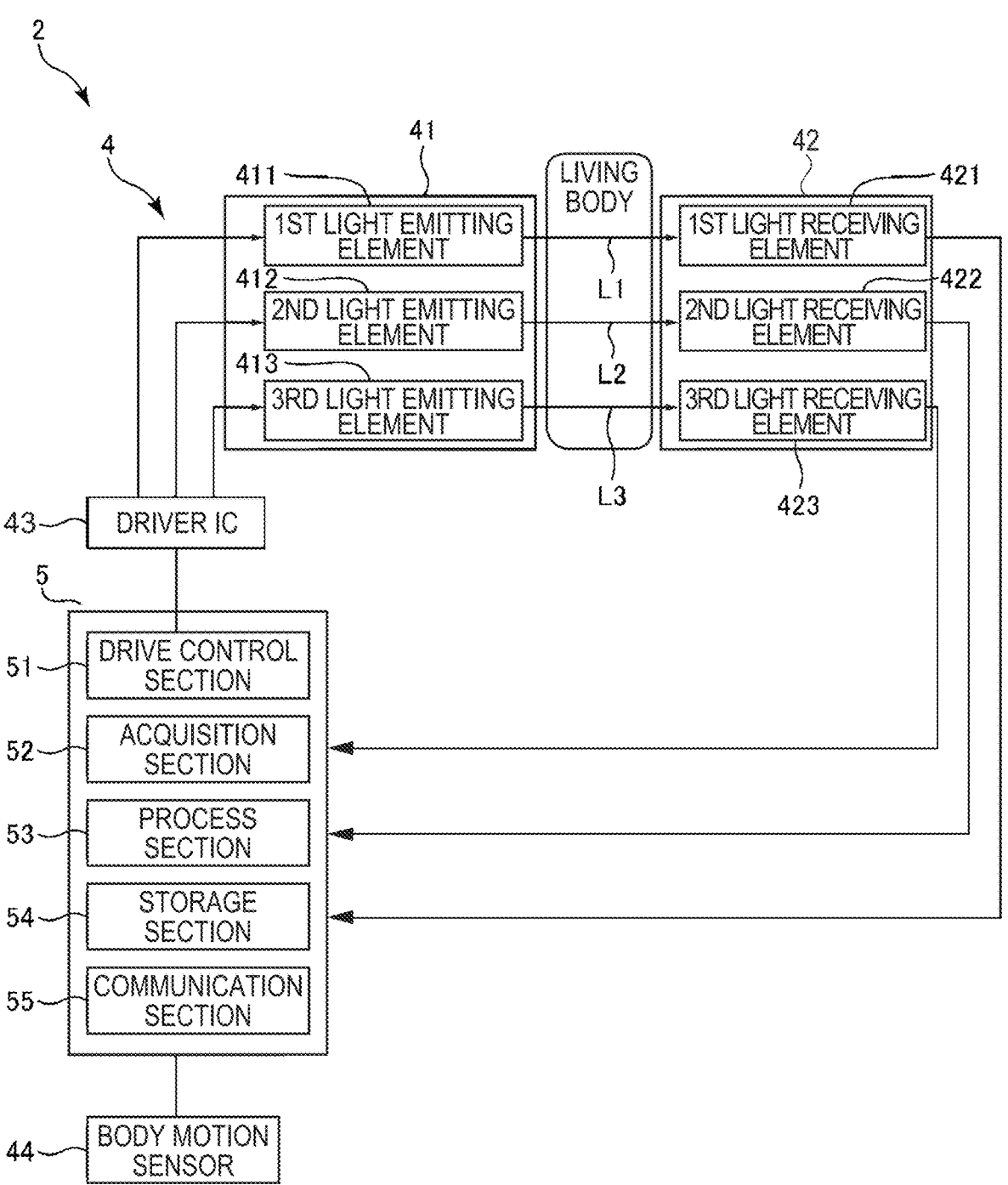
FIG. 2 is a functional block diagram of the biometric information acquisition device shown in FIG. 1.
Figure 3:
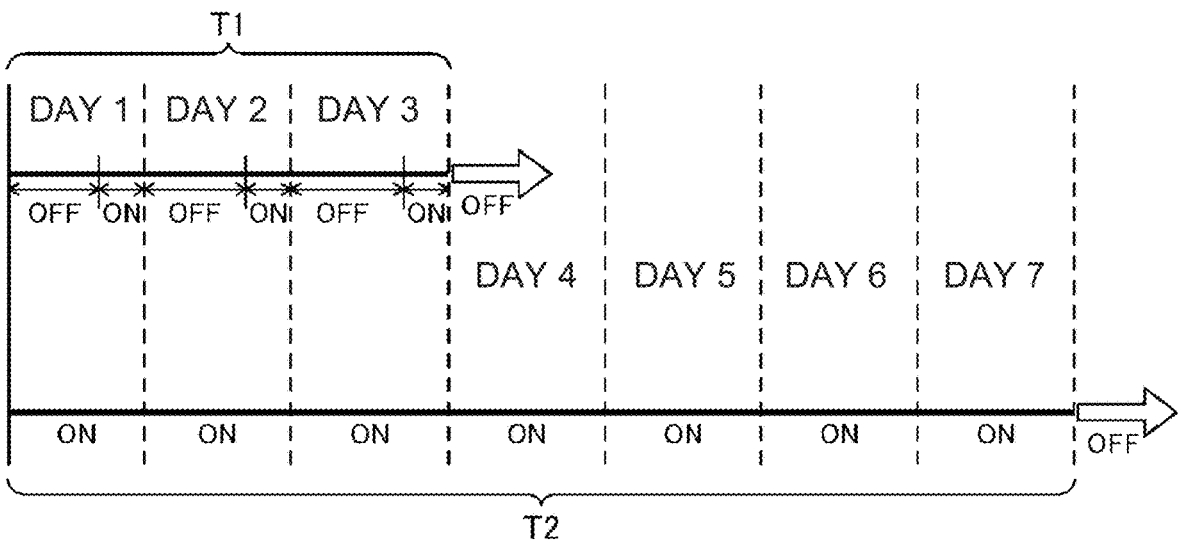
FIG. 3 is a time chart for explaining the first time period T1 and the second time period T2.

FIG. 1 is a cross-sectional view of a biometric information acquisition device of the present disclosure. FIG. 2 is a functional block diagram of the biometric information acquisition device shown in FIG. 1. FIG. 3 is a time chart for explaining the first time period T1 and the second time period T2.

A biometric information acquisition device 2 shown in FIG. 1 is a wearable device that obtains biometric information of the user in a state where it is worn on a living body of the user.

The biometric information acquisition device 2 obtains first biometric information, which is based on first information and second information (to be described later), and second biometric information, which is based on third information (to be described later). That is, the biometric information acquisition device 2 measures the first and second biometric information.

The first biometric information and the second biometric information obtained by the biometric information acquisition device 2 are sent from the biometric information acquisition device 2 to a gateway terminal device, such as a smartphone or a tablet terminal, a server, or the like, for example, via wireless communication means, such as Bluetooth (registered trademark), Wi-Fi, or the like.

However, it is not limited to this configuration. The biometric information acquisition device 2 may be configured to store the biometric information without communicating with the gateway terminal device or the server. In this case, it is desirable that the biometric information acquisition device 2 has a display device that displays the biometric information.

As shown in FIG. 1, the biometric information acquisition device 2 has a wearing belt 3 that is worn on the living body, and a device main body 4.

The target area on which the wearing belt 3 is worn is not particularly limited, but includes, for example, fingers, wrists, arms, toes, ankles, neck, ears, head, abdomen, chest, and other front surfaces of the living body.

The device main body 4 is provided to the inside of the wearing belt 3, and faces the living body in a state where the wearing belt 3 is worn on the living body. At this time, the device main body 4 may be in contact with the living body, or it may be in close proximity but not in contact with the living body.

As shown in FIG. 2, the device main body 4 has a light emitting unit 41, a light receiving unit 42, a driver IC 43, a control unit 5, a body motion sensor 44, and a housing 40 that houses these components. The housing 40 has a window section (not shown) that transmits light emitted from the light emitting unit 41. The window section can be configured by, for example, an opening provided in the housing 40 or a transparent plate having optical transparency.

The light emitting unit 41 has a first light emitting element 411, a second light emitting element 412, and a third light emitting element 413. The first light emitting element 411 emits red light L1 toward the living body. The second light emitting element 412 emits infrared light L2 toward the living body. The third light emitting element 413 emits green light L3 toward the living body.

For example, a laser light source, a light emitting device, or the like can be used as the first light emitting element 411, the second light emitting element 412, and the third light emitting element 413.

The light receiving unit 42 has a first light receiving element 421, a second light receiving element 422, and a third light receiving element 423.

The first light receiving element 421 receives reflected light of the red light L1, which was emitted from the first light emitting element 411 and reflected by the living body. In other words, the first light receiving element 421 receives the red light L1 that has passed through the living body. Here, "passed through the living body" means "transmitted through the living body" or "reflected by the living body". In other words, the first light receiving element 421 receives the red light L1 that is emitted from the first light emitting element 411 and is irradiated to the living body and that has passed through the living body.

The second light receiving element 422 receives reflected light of the infrared light L2, which was emitted from the second light emitting element 412 and reflected by the living body. In other words, the second light receiving element 422 receives the infrared light L2 that has passed through the living body.

The third light receiving element 423 receives reflected light of the green light L3, which was emitted from the third light emitting element 413 and reflected by the living body. In other words, the third light receiving element 423 receives the green light L3 that has passed through the living body.

For example, a phototransistor, a photodiode, or the like can be used as the first light receiving element 421, the second light receiving element 422, and the third light receiving element 423.

The first light receiving element 421, the second light receiving element 422, and the third light receiving element 423 each output an electrical signal (received light information) corresponding to the received light amount in the specified wavelength range, that is, to the intensity of the received light amount. Specifically, the first light receiving element 421 outputs an electric signal with an intensity corresponding to the received light amount of the red light L1 that has passed through the living body, the second light receiving element 422 outputs an electric signal with an intensity corresponding to the received light amount of the infrared light L2 that has passed through the living body, and the third light receiving element 423 outputs an electric signal with an intensity corresponding to the received light amount of the green light L3 that has passed through the living body.

The electric signals (received light information) corresponding to the received light amount of each type of light obtained by the light receiving unit 42 are sent to the control unit 5, and they are processed in a predetermined manner that corresponds with the first biometric information and second biometric information to be obtained.

As described above, the light emitting unit 41 and the light receiving unit 42 constitute a reflective optical sensor. However, it is not limited to this configuration. The light emitting unit 41 and the light receiving unit 42 may constitute a transmissive optical sensor. In this case, the light emitting unit 41 and the light receiving unit 42 face each other across the living body, and are configured to receive light that has passed through the living body, that is, that was transmitted through the living body.

The body motion sensor 44 detects movement of the user and is comprised of, for example, an acceleration sensor, a gyro sensor, a barometric pressure sensor, an electrostatic capacitance sensor, a geomagnetic sensor, a global positioning system (GPS) receiver, and the like. The body motion sensor 44 obtains body motion information, and the obtained body motion information is sent to the control unit 5.

As shown in FIG. 2, the control unit 5 includes a drive control section 51, an acquisition section 52, a process section 53, a storage section 54, and a communication section 55.

The drive control section 51 generates a control signal that drives the driver IC 43 in accordance with a program stored in the storage section 54, and outputs this control signal to the driver IC 43. The driver IC 43 generates drive signals to drive the first light emitting element 411, second light emitting element 412, and third light emitting element 413 independently based on the control signals input from the drive control section 51. In other words, the driver IC generates power signals. By this, the first light emitting element 411, the second light emitting element 412, and the third light emitting element 413 can be driven under desired conditions.

The acquisition section 52 obtains first information based on a light amount of the red light L1 received by the first light receiving element 421, second information based on a light amount of the infrared light L2 received by the second light receiving element 422, and third information based on a light amount of the green light L3 received by the third light receiving element 423.

The first information is temporal information about the light amount of the red light L1 that has received by the first light receiving element 421. The second information is temporal information about the light amount of the infrared light L2 that has received by the second light receiving element 422. The third information is temporal information about the light amount of the green light L3 that has received by the third light receiving element 423.

The first information, the second information, and the third information obtained by the acquisition section 52 are stored in the storage section 54.

The process section 53 obtains the first biometric information and the second biometric information in accordance with a program stored in the storage section 54.

The process section 53 performs a process of obtaining information about the blood oxygen saturation level, that is, the first biometric information, based on the first information and the second information. Specifically, the process section 53 performs a process that determines a redness level of the user's blood based on the received light amount of the red light L1 and the received light amount of the infrared light L2, and then estimates a ratio of hemoglobin that is bound to oxygen. By this, the information about the blood oxygen saturation level can be obtained.

The process section 53 also performs a process to obtain information about the pulse wave, that is, the second biometric information, based on the third information. Specifically, the process section 53 obtains temporal information about a blood flow volume that changes with the pulsation of the user's heart based on the received light amount of the green light L3. In other words, the process section 53 obtains the information about the pulse wave.

The first biometric information and the second biometric information obtained by the process section 53 are stored in the storage section 54. The process section 53 also determines whether the user is sleeping or not based on the body motion information obtained by the body motion sensor 44. In accordance with the determination result, the drive control section 51 generates the control signal for driving the driver IC 43.

The storage section 54 stores various programs such as a program to be executed by the drive control section 51, a program to be executed by the acquisition section 52, a program to be executed by the process section 53, and the like. The first biometric information and the second biometric information obtained by the process section 53 are stored in the storage section 54.

The communication section 55 has a function of sending the first biometric information and the second biometric information by communicating with other devices, for example, a gateway terminal device, a server, or the like by using various networks.

A central processing unit (CPU), a graphics processing unit (GPU), a digital signal processor (DSP), and the like can be used as the drive control section 51, the acquisition section 52, and the process section 53. Note that instead of these processors executing software, all or part of the above functions may be realized by a field programmable gate array (FPGA), an application specific integrated circuit (ASIC), or the like.

The storage section 54 serves as a work region for the drive control section 51, the acquisition section 52, and the process section 53. This function can be realized by memory such as a RAM, a ROM, and the like, or a hard disk drive (HDD) and the like. The processes in the drive control section 51, the acquisition section 52, and the process section 53 may involve reading and writing information stored in the storage section 54. Each process performed by the drive control section 51, the acquisition section 52, and the process section 53 is executed in accordance with various data and programs stored in the storage section 54.

The communication section 55 is comprised of, for example, an I/O interface. The communication standard employed by the I/O interface is not particularly limited, and includes, for example, a personal area network (PAN) such as a Bluetooth (registered trademark) network, a local area network (LAN) such as a Wi-Fi (registered trademark) network, and the like.

Such biometric information acquisition device 2 is not particularly limited to the terminals with the above functions, but includes, for example, wearable watches, wearable rings, wearable displays, smart glasses, wearable cameras, wearable speakers, earphones, headphones, and smart wear, and the like.

Although the configuration described above is described in which the biometric information acquisition device 2 obtains the first biometric information (information about the blood oxygen saturation level) and the second biometric information (information about the pulse wave) as the biometric information, the present disclosure is not limited to this.

In other words, the biometric information acquisition device 2 in this embodiment does not preclude having a function to obtain (measure) third biometric information other than the first biometric information and the second biometric information. The third biometric information includes, for example, body temperature, pulse rate, electrocardiogram, blood oxygen level, blood glucose level, blood pressure, degree of sweating, respiration rate, expired air component, bone density, sleep duration, urination duration, urination frequency, number of steps, eye movement, body weight, muscle mass, body fat ratio, BMI value, and the like. The biometric information acquisition device 2 can be capable of measuring one or two or more of these items.

In general, in order to accurately obtain the first biometric information, which is the information about the blood oxygen saturation level, it is desirable to drive the first light emitting element 411 and the second light emitting element 412 for a period of several days, and to obtain the information for several days. In order to accurately obtain the second biometric information, which is the information about the pulse wave, it is also desirable to drive the third light emitting element 413 for a period of several days, and to obtain the information for several days. In the related art method, the light emitting unit, which corresponds to light emitting unit 41, continues to be driven even after the information for several days has been obtained. Therefore, there is a problem that the power consumption increases to higher than necessary.

In contrast, in the biometric information acquisition device 2, the drive control section 51 performs at least one of the first process and the second process described below. Therefore, it is possible to reduce the power consumption compared to the related art method.

As shown in FIG. 3, the first process is a process that stops the light emission of the first light emitting element 411 and the second light emitting element 412 when the measurement period for measuring the first biometric information reaches a first time period T1. The first time period T1 is a period of time that is sufficient to accurately obtain the first biometric information, and is desirably between 2 to 5 days, and is more desirably between 3 to 4 days, for example. Particularly, the first biometric information can be accurately obtained by setting the first time period T1 to three days or more.

The measurement of the first biometric information should desirably be measured during the user's sleeping period. By this, the first biometric information can be measured accurately. The sleep of the user can be detected based on a detection value of the body motion sensor 44.

For example, if the body motion sensor 44 detects that the biometric information acquisition device 2 is stationary for a predetermined time period or higher, the drive control section 51 determines that the user is sleeping, and the biometric information acquisition device 2 measures the first biometric information. On the other hand, if the drive control section 51 determines that the user is not sleeping, the drive control section 51 stops the light emission of the first light emitting element 411 and the second light emitting element 412. By this, the first biometric information can be measured more accurately and contributes to further reduction of power consumption.

The second process is a process that stops the light emission of the third light emitting element 413 when the measurement period for measuring the second biometric information reaches a second time period T2. The second time period T2 is a period of time that is sufficient to accurately obtain the second biometric information, and is desirably between 3 to 9 days, and is more desirably between 5 to 7 days, for example. Particularly, the second biometric information can be accurately obtained by setting the second time period T2 to four days or more.

The magnitude relationship between the first time period T1 and the second time period T2 is not particularly limited, but T1≤T2 is desirable, T1<T2 is more desirable, 1.25T1≤T2 is further desirable, and 1.5T1≤T2≤10T1 is particularly desirable. When these conditions are satisfied, the effects of the present disclosure described later can be achieved more significantly and more reliably.

The measurement in the second time period T2 is desirable to be done continuously, that is, day and night, at all times. By this, the second biometric information can be measured more accurately and the second time period T2 can be set as short as possible, and it contributes to further reduction of power consumption.

As described above, the biometric information acquisition device 2 includes the light emitting unit 41 having the first light emitting element 411 that emits red light L1 toward a living body, the second light emitting element 412 that emits infrared light L2 toward the living body, and the third light emitting element 413 that emits green light L3 toward the living body; the light receiving unit 42 having the first light receiving element 421 that receives the red light L1 that passed through the living body, the second light receiving element 422 that receives the infrared light L2 that passed through the living body, and the third light receiving element 423 that receives the green light L3 that passed through the living body; the acquisition section 52 that obtains first information based on a light amount of the red light L1 received by the first light receiving element 421, second information based on a light amount of the infrared light L2 received by the second light receiving element 422, and third information based on a light amount of the green light L3 received by the third light receiving element 423; and the drive control section 51 that controls drive and stop of each of the first light emitting element 411, the second light emitting element 412, and the third light emitting element 413; wherein the biometric information acquisition device measures first biometric information based on the first information and the second information, and second biometric information based on the third information. The drive control section 51 performs at least one of the first process, which stops light emission of the first light emitting element 411 and the second light emitting element 412 when a measurement period for measuring the first biometric information reaches the first time period T1, and the second process, which stops the light emission of the third light emitting element 413 when the measurement period for measuring the second biometric information reaches the second time period T2. By this, power consumption of the biometric information acquisition device 2 can be reduced.

Note that of the first and second processes, the drive control section 51 may perform only the first process, only the second process, or both the first process and the second process. In any of these situations, the power consumption can be reduced compared to the related art method.

In addition, the drive control section 51 may have a first mode that performs only the first process, a second mode that performs only the second process, and a third mode that performs both the first process and the second process, and may be capable of selecting the first mode, the second mode, and the third mode by a mode selection section (not shown), which is included in the biometric information acquisition device 2. In this case as well, the power consumption can be reduced compared to the related art method.

The first biometric information is information about the blood oxygen saturation level, and the second biometric information is information about the pulse wave. The information about the blood oxygen saturation level and the pulse wave have a relatively high need for measurement or are measured relatively frequently and are types of information that are relatively important for understanding health status. Therefore, if the biometric information acquisition device 2 is configured to obtain information about the blood oxygen saturation level and the pulse wave, the effects of the present disclosure can be more significantly achieved, and the scope of application of the biometric information acquisition device 2 that can benefit from the present disclosure is also broadened.

The second time period T2 is longer than the first time period T1. That is, T1<T2. By this, the information about the blood oxygen saturation level and the pulse wave can be measured each more accurately, and also contributes to reduce the power consumption. The present disclosure is not limited to this, and the second time period T2 may be the same as or shorter than the first time period T1. Desired magnitude relationship between T1 and T2 described above is not limited to a first case where the first biometric information is information about the blood oxygen saturation level and the second biometric information is information about the pulse wave. For example, it can be applied to any of the following cases: a second case where the first biometric information is information about the blood oxygen saturation level and the second biometric information is information about an item other than the pulse wave; a third case where the first biometric information is information about an item other than the blood oxygen saturation level and the second biometric information is information about the pulse wave; and a fourth case where the first biometric information is information about an item other than the blood oxygen saturation level and the second biometric information is information about an item other than the pulse wave.

The first time period T1 desirably includes a sleeping period of at least three days. By this, more accurate first biometric information can be obtained.

Note that this configuration can be applied not only to the first case but also to the second case, the third case, and the fourth case.

Further, the biometric information acquisition device 2 has the body motion sensor 44 as a sensor to detect the sleep of the user who is the wearer, and the drive control section 51 drives the first light emitting element 411 and the second light emitting element 412 during the sleeping period in the first time period T1, and stops the light emission of the first light emitting element 411 and the second light emitting element 412 except for the sleeping period in the first time period T1. By this, the first biometric information can be measured more accurately and contributes to further reduction of power consumption.

Note that this configuration can be applied not only to the first case but also to the second case, the third case, and the fourth case.

The second time period T2 is at least four consecutive days. By this, more accurate second biometric information can be obtained.

Note that this configuration can be applied not only to the first case but also to the second case, the third case, and the fourth case.

Further, it is desirable that the first time period T1 and the second time period T2 can be settable. In other words, it is desirable that the first time period T1 and the second time period T2 can be appropriately changed by the wearer. By this, more appropriate first biometric information and second biometric information can be obtained.

The first time period T1 and the second time period T2 are set, for example, by touch operation from a setting input screen (not shown) of the biometric information acquisition device 2. Note that the configuration is not limited to this, for example, the biometric information acquisition device 2 may be configured to set the first time period T1 and the second time period T2 via a device that communicates with the biometric information acquisition device 2.

Although the biometric information acquisition device of the present disclosure is described with reference to the embodiments shown in the figures, the present disclosure is not limited to these embodiments, and each section of the biometric information acquisition device of the present disclosure can be replaced with an arbitrary configuration that can exhibit the same function. Further, any structure may be added to the biometric information acquisition device of the present disclosure.

What is claimed is:

1. A biometric information acquisition device, comprising:

a light emitting unit having a first light emitting element that emits red light toward a living body of a wearer of the biometric information acquisition device, a second light emitting element that emits infrared light toward the living body, and a third light emitting element that emits green light toward the living body;

a light receiving unit having a first light receiving element that receives the red light that passed through the living body, a second light receiving element that receives the infrared light that passed through the living body, and a third light receiving element that receives the green light that passed through the living body; and circuitry that:

obtains first information based on a light amount of the red light received by the first light receiving element, second information based on a light amount of the infrared light received by the second light receiving element, and third information based on a light amount of the green light received by the third light receiving element;

controls drive and stop of each of the first light emitting element, the second light emitting element, and the third light emitting element, wherein the biometric information acquisition device measures:

first biometric information only during a sleeping period of the wearer based on the first information and the second information, and second biometric information during both the sleeping period of the wearer and a non-sleeping period of the wearer based on the third information, the first biometric information is information about blood oxygen saturation level of the wearer, and the second biometric information is information about pulse wave of the wearer; and performs at least one of:

a first process, which stops light emission of the first light emitting element and the second light emitting element when a measurement period for measuring the first biometric information reaches a first time period T1, and a second process, which stops light emission of the third light emitting element when the measurement period for measuring the second biometric information reaches a second time period T2, wherein the second time period T2 is longer than the first time period T1.

2. The biometric information acquisition device according to claim 1, wherein the first time period T1 includes the sleeping period of at least three days.

3. The biometric information acquisition device according to claim 2, further comprising:

a motion sensor that detects sleep of the wearer, wherein the circuitry drives the first light emitting element and the second light emitting element during the sleeping period in the first time period T1, and stops the light emission of the first light emitting element and the second light emitting element except during the sleeping period in the first time period T1.

4. The biometric information acquisition device according to claim 1, wherein the second time period T2 is at least 4 consecutive days.

5. The biometric information acquisition device according to claim 1, wherein the first time period T1 and the second time period T2 are settable.

* * * * *